United States Patent [19]

Steiner et al.

[11] 4,256,895
[45] Mar. 17, 1981

[54] PROCESS FOR DISPLACING NUCLEAR IODINE WITH CHLORINE IN IODIPYRIDINES

[75] Inventors: Edwin C. Steiner; G. Edwin Vrieland, both of Midland, Mich.

[73] Assignee: The Dow Chemical Company, Midland, Mich.

[21] Appl. No.: 72,705

[22] Filed: Sep. 4, 1979

[51] Int. Cl.$^3$ .......................................... C07D 213/04
[52] U.S. Cl. .................................................... 546/345
[58] Field of Search ..................... 546/345; 260/650 R

[56] References Cited

U.S. PATENT DOCUMENTS 4,158,674  6/1979  Morris .............................. 260/650 R Primary Examiner—Alan L. Rotman
Attorney, Agent, or Firm—Michael L. Glenn

[57] ABSTRACT

The nuclear iodine substituents borne by an iodopyridine are displaced by introducing gaseous chlorine into the mixture at a temperature of from about 100° C. to about 250° C. The displacement of iodine produces chloropyridines, which can then be conveniently separated from the liberated iodine by conventional methods such as distillation.

3 Claims, No Drawings

PROCESS FOR DISPLACING NUCLEAR IODINE WITH CHLORINE IN IODIPYRIDINES

BACKGROUND OF THE INVENTION

This invention relates to the displacement of nuclear iodine substituents from an iodopyridine with gaseous chlorine.

The prior art suggests that the treatment of pyridine bearing nuclear iodine substituents with gaseous (molecular) chlorine does not displace the iodine substituents. British Pat. No. 259,960 teaches that nuclear iodine substituents on pyridines are not displaced by chlorine, but instead pyridyl iodochlorides are obtained.

SUMMARY OF THE INVENTION

This invention is a method for displacing with chlorine moieties nuclear iodine substituents borne by an iodopyridine compound which comprises introducing gaseous chlorine into a liquid medium containing the iodopyridine compound at a temperature of from about 100° C. to about 250° C., so as to displace one or more iodine substituents and produce chloropyridine compounds. The resulting chloropyridine compounds are then separated from the displaced iodine.

Surprisingly, the practice of the instant process replaces nuclear iodine substituents with chlorine. This replacement improves the purity of chloropyridines, where corresponding pyridine compounds are present having an iodine substituent in place of at least one chlorine.

DETAILED DESCRIPTION OF THE INVENTION

The iodopyridine is a compound comprising a pyridyl moiety which bears at least one iodine substituent attached to a carbon atom of the pyridyl moiety and other substituents which do not substantially hinder the displacement of iodine with chlorine. It is desirable that the pyridyl moiety bears only one iodine substituent. The preferred nuclear substituents in addition to the iodine moiety include chlorine, bromine and hydrogen. Some of these other nuclear substituents, in particular bromine, will also exchange with chlorine.

The iodopyridines can be a single compound or a mixture of suitable compounds. The iodopyridine can also be present in a mixture with other compounds not bearing iodine substituents exchangeable with chlorine, such as chloropyridines. Especially preferred iodopyridines are those comprising a pyridyl moiety which bears one iodine substituent, at least one chlorine substituent and a remaining number of hydrogen substituents on the carbon atoms of the pyridine ring. These especially preferred iodopyridines include dichloroiodopyridine, trichloroiodopyridine, tetrachloroiodopyridine and the like.

The iodopyridine should be present in the liquid phase when the gaseous chlorine is introduced. Diluents inert in the reaction, such as chlorinated hydrocarbons, can optionally be employed. The chlorine can conveniently be sparged through or otherwise placed in intimate contact with the reaction medium. Agitation of the medium during addition of the chlorine is desirable.

The chlorine can be continuously or batchwise introduced into the medium during the replacement reaction. If the iodopyridine is present as a minor impurity in a chloropyridine medium, the chlorine is conveniently introduced continuously during the initial phases of the reaction and the addition is terminated after several minutes when the medium is substantially saturated with chlorine. The displacement reaction continues for several minutes after the addition of chlorine is terminated. The total amount of chlorine introduced into the medium is advantageously a large molar excess relative to the iodine to be replaced.

The rapidity of replacement of iodine with chlorine is dependent on the temperature during contact, the particular iodopyridine involved, and numerous other factors. Desirably, the temperature of the medium during the replacement reaction is at least about 130° C., preferably at least about 150° C., to promote rapid reaction. Lower temperatures are operable as long as the iodopyridine is present in liquid phase, but generally result in an uneconomically slow rate of reaction. The maximum reaction temperature is limited by the temperature at which substantial thermal degradation of reactants or products occurs and the temperature at which the vapor pressure of reactants and products becomes inconveniently large. Typically, the temperature of the medium during the replacement reaction is preferably no greater than about 250° C., more preferably no greater then about 200° C.

The pressure during the replacement reaction is not critical. Conveniently, atmospheric pressure is employed. However, it can be advantageous to employ superatmospheric pressure to maintain the iodopyridine and chloropyridine in the liquid phase during the reaction.

The presence of iron in contact with the medium may facilitate the addition of chlorine and liberated iodine to the pyridinic ring. Therefore, it is desirable to utilize a reaction vessel having some material other than iron in contact with the medium such as a glass-lined reactor. It is also desirable to remove iron-derived chlorination catalysts, such as ferric chloride or finely divided iron, from the reaction medium prior to the replacement reaction. Iron-derived catalysts can be removed by conventional methods, such as flash distillation of the medium prior to introducing chlorine for the replacement reaction.

The replacement of iodine with chlorine by the practice of the instant method does not require irradiation of the medium to proceed. However, it is operable and convenient to expose the medium to visible light and to carry out the reaction in a vessel having a transparent region through which the medium can be observed. The progression of the reaction can then be gauged by a color change in the medium to a red or orange color indicating the presence of free iodine released in the replacement reaction.

After the iodine has been released, the iodine can be separated from the chloropyridine in any convenient manner. Typically, the iodine can be readily removed from the chloropyridine by distillation of the mixture. Advantageously, the replacement reaction with chlorine and the subsequent separation step can be repeated with the distilled predominantly chloropyridine product to remove residual iodine.

The specific examples that follow illustrate the invention, but are not to be taken as limiting its scope.

EXAMPLE 1

A mixture of 15 grams of 2,3,5,6-tetrachloropyridine (TCP) and 3.73 grams of 3,5,6-trichloro-2-iodopyridine (TCIP) is introduced into a glass reaction vessel. A gas mixture of nitrogen and chlorine is bubbled slowly and continuously into the liquid mixture of substituted pyridines as the temperature is slowly increased from 100° C. to 190° C. At a temperature of 130° C., the mixture first appears red in color. Samples of the mixture are periodically removed, thereafter, and analyzed by conventional techniques to determine the composition of the mixture. The time of the sampling, the temperature of the mixture and weight percent of each component are tabulated in Table I.

TABLE I

| Sample No. | Time (hours) | Temperature (°C.) | TCP (Wt. %) | TCIP (Wt. %) |
|---|---|---|---|---|
| 1 | 0 | 130 | 81.47 | 18.53 |
| 2 | 0.75 | 163 | 91.29 | 8.71 |
| 3 | 1.75 | 190 | 98.22 | 1.78 |
| 4 | 2.75 | 190 | 99.61 | 0.39 |

EXAMPLE 2

In a manner otherwise similar to Example 1, chlorine in a mixture with nitrogen gas is bubbled slowly and continuously into liquid 2,3,5,6-tetrachloro-4-iodopyridine at a temperature of 195° C. Samples of the reaction mixture are removed hourly and analyzed by conventional techniques to determine the composition of the mixture. The time elapsed from the initiation of bubbling to the taking of the sample and the weight percent of each component is tabulated in Table II.

TABLE II

| Time (hours) | Tetrachloro-iodopyridine (Wt. Percent) | Pentachloro-pyridine (Wt. Percent) |
|---|---|---|
| 1 | 76.13 | 23.90 |
| 2 | 61.59 | 38.41 |
| 3 | 41.69 | 58.31 |

What is claimed is:

1. A process for replacing with chlorine moieties nuclear iodine substituents borne by an iodopyridine compound comprising the steps of:
    (a) introducing gaseous chlorine into a liquid medium containing trichloroiodopyridine or tetrachloroiodopyridine at a temperature of from about 100° C. to about 250° C., so as to displace the iodine substituent from the iodopyridine compound and thereby produce the corresponding chloropyridine compound; and
    (b) separating the chloropyridine compound from the displaced iodine.

2. The process as defined in claim 1 wherein the temperature during introduction of gaseous chlorine is from about 130° C. to about 200° C.

3. The process as defined in claim 1 or 2 further comprising the step of substantially completely removing iron or ferric chloride compounds from contact with the iodopyridine prior to introducing the chlorine.

* * * * *